United States Patent [19]

Knowles et al.

[11] 4,261,919
[45] Apr. 14, 1981

[54] CATALYTIC ASYMMETRIC HYDROGENATION

[75] Inventors: William S. Knowles, St. Louis; Milton J. Sabacky, Ballwin, both of Mo.

[73] Assignee: Monsanto Company, St. Louis, Mo.

[21] Appl. No.: 939,570

[22] Filed: Sep. 5, 1978

Related U.S. Application Data

[63] Continuation of Ser. No. 122,116, Mar. 8, 1971, abandoned, which is a continuation-in-part of Ser. No. 36,471, May 11, 1970, abandoned, which is a continuation-in-part of Ser. No. 758,603, Sep. 9, 1968, abandoned.

[51] Int. Cl.$^3$ .................. C07C 103/50; C07C 103/84
[52] U.S. Cl. ...................... 260/465 D; 260/326.13 A; 260/340.5 R; 260/347.3; 549/76; 560/22; 560/38; 562/437; 562/443; 562/445; 562/446; 562/447; 562/561; 562/565; 562/571; 562/575
[58] Field of Search .............. 562/443, 445, 575, 437, 562/446, 561, 565, 571, 447; 260/465 D, 326.13 A, 340.5 R, 347.3; 549/76; 560/22, 38

[56] References Cited
U.S. PATENT DOCUMENTS 3,849,480   11/1974   Knowles et al. ..................... 260/490

OTHER PUBLICATIONS

Horner et al., Tetrahedron Letters, vol. 37 (1968) pp. 4023-4026.
Horner et al., Angewandte Chemi, vol. 7 (1968) p. 942.
Knowles et al., Chem. Comm, vol. 22 (1968) pp. 1445-1446.

Primary Examiner—Richard Raymond
Attorney, Agent, or Firm—Robert E. Wexler

[57] ABSTRACT

Process for the homogeneous catalytic hydrogenation of β-substituted-α-acylamido-acrylic acids which yields, after hydrogenation, an optically active mixture. The process comprises the hydrogenation of β-substituted-α-acylamidoacrylic acids in the presence of an optically active coordinated metal complex hydrogenation catalyst, in which the metal is selected from the group consisting of rhodium, iridium, ruthenium, osmium, palladium and platinum.

This process is a generalized process for any asymmetric hydrogenation of β-substituted-α-acylamido-acrylic acids in which one α-amino acid enantiomorph is the desired end-product. It is especially useful for the preparation of α-amino acids found in nature which possess optical activity and which have a hydrogen attached to the asymmetric center.

This invention also relates to new optically active coordinated metal complex hydrogenation catalysts.

10 Claims, No Drawings

CATALYTIC ASYMMETRIC HYDROGENATION

This is a continuation of application Ser. No. 122,116, filed Mar. 8, 1971, now abandoned, which in turn is a continuation-in-part of our copending application, Ser. No. 36,471 filed May 11, 1970, now abandoned, which is a continuation-in-part of our copending application Ser. No. 758,603, filed Sept. 9, 1968, now abandoned.

When an olefin, which in its saturated form is optically active, is hydrogenated, the usual resultant product is optically inactive mainly because an equal amount of both enantiomorphs (racemic mixture) are formed. To obtain the desired enantiomorph, the mixture must be separated into its optical components. This procedure is laborious, expensive, and often results in the destruction of the undesired enantiomorph. Due to these difficulties, increased attention has been placed on asymmetric synthesis in which one of the enantiomorphs is obtained in major amounts.

It has now been found that excellent yields of a desired enantiomorph of α-amino acids can be achieved from those olefinic compounds that are β-substituted-α-acylamidoacrylic acids and/or their salts by hydrogenation of the olefinic bond in the presence of an optically active coordinated metal complex hydrogenation catalyst. Such a reaction is illustrated by the following equation: (wherein the β-substituent is phenyl)

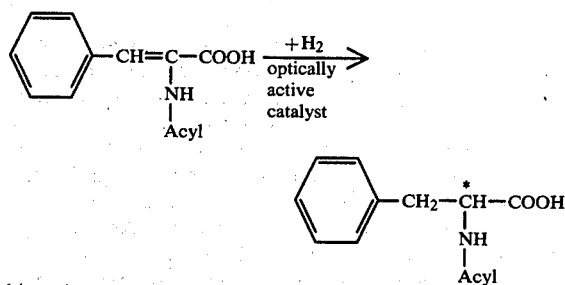

*shows the asymmetrical carbon

The β-substituent can be exemplified by such groups as hydrogen, alkyl, substituted alkyl, aryl, substituted aryl, aralkyl, amino, benzylamino, dibenzylamino, nitro, carboxyl and carboxyl ester, and the like. Those skilled in the art will recognize that the β-substituent can be selected from a large number of groups and that this is limited only by the α-amino acid that is the desired end-product.

Exemplary α-amino acids whose enantiomorphs can be expeditiously prepared in accordance with the process of this invention are alanine, p-chlorophenylalanine, tryptophane, phenylalanine, 3-(3,4-dihydroxyphenyl)-alanine, 5-hydroxytryptophane, lysine, histidine, tyrosine, leucine, glutamic acid and valine.

The acyl group can be substituted or unsubstituted acyl and can be exemplified by such groups as acetyl, benzoyl, formyl, propionyl, butyryl, toluyl, nitrobenzoyl, or other acyl ariants utilized as blocking groups in peptide synthesis, etc.

It is preferred that such catalytic hydrogenation of the β-substituted-α-acylamido-acrylic acids be conducted in the presence of a base.

β-substituted-α-acylamido-acrylic acids and/or their salts are precursors of the substituted and unsubstituted alanines.

The compounds represented by the following structural formula provide excellent results with the process of this invention and therefore represent compounds particularly amenable to the present invention.

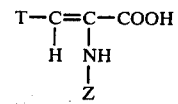

wherein, T is selected from the group consisting of hydrogen, carboxyl, unsubstituted and substituted alkyl, thienyl, β-indolyl, β-imidazolyl, furyl, piperonyl and

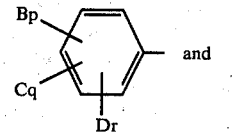

B, C and D are independently selected from the group consisting of hydrogen, alkyl, carboxyl, hydroxyl (and their metal salts), alkoxy, halogen, acyloxy, aryloxy, aralkyloxy, amino, alkyl amino, nitro, cyano, Z is selected from the group consisting of substituted or unsubstituted acyl, as described above, and p, q and r are integers of from 0 to 5 provided that the sum of p, q and r does not exceed 5.

A particularly preferred embodiment, which is also illustrative of the process of this invention, is the preparation of the substituted and unsubstituted phenylalanines by the catalytic asymmetric hydrogenation of the present invention. Unsaturated precursors of such α-amino acids can be prepared by the Erlenmeyer azlactone synthesis, wherein a substituted or unsubstituted benzaldehyde is reacted with an acylglycine, such as acetylglycine, and acetic anhydride to form the azlactone which is hydrolyzed to form the unsaturated precursor. Such a reaction is illustrated by the following equations (utilizing benzaldehyde and acetylglycine as illustrative reactants):

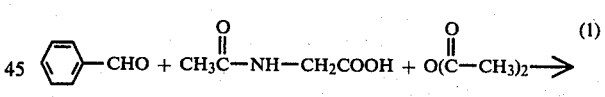

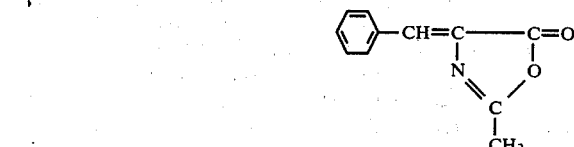

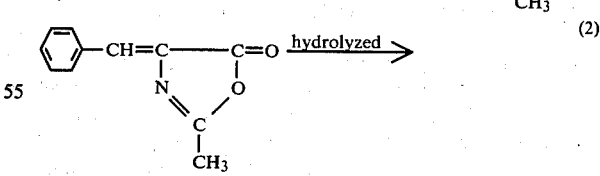

In such reactions the substituents on the phenyl group can be selected from a large number of groups and is limited only by the phenylalanine that is the desired end-product. Furthermore, it may occur that such substituent groups are themselves precursors of substituents that are desired in the end-product that can readily be converted to such desired substituents. For instance, if the substituted benzaldehyde is vanillin and one wishes to prepare 3-(3,4-dihydroxyphenyl)-alanine the unsaturated precursor might be α-acetamido-4-hydroxy-3-methoxy-cinnamic acid which would provide N-acetyl-3-(4-hydroxy-3-methoxyphenyl)-alanine upon hydrogenation which can then be converted to 3-(3,4-dihydroxyphenyl)-alanine by simple hydrolysis.

The L enantiomorph of such phenylalanines are particularly desirable. For instance, 3-(3,4-dihydroxyphenyl)-L-alanine (L-DOPA) is well known for its usefulness in treating the symptoms of Parkinson's Disease. Likewise, L-phenylalanine has found use as an intermediate in the preparation of the alkyl esters of L-aspartyl-L-phenylalanine which have been recently recognized as excellent synthetic sweeteners.

The optically active hydrogenation catalysts useful in this invention are soluble coordination complexes comprising a metal selected from the group consisting of rhodium, iridium, ruthenium, osmium, palladium and platinum, in combination with at least one optically active phosphine or arsine ligand. These catalysts are soluble in the reaction mass and are therefore referred to as "homogeneous" catalysts.

The phosphine or arsine ligand can be, for instance, of the formula $AR^5R_6R^7$ wherein A is phosphorus or arsenic and $R^5$, $R^6$ and $R^7$ are each independently selected from the group consisting of hydrogen; alkyl or alkoxy, having at least one carbon atom and a maximum of 12 carbon atoms; substituted alkyl said substitution selected from the group consisting of amino, carbonyl, aryl, nitro and alkoxy, said alkoxy having a maximum of 4 carbon atoms; aryl; aryloxy; phenyl; substituted phenyl, said substitution selected from the group consisting of alkoxy and alkyl, hydroxy, aryloxy, amino and nitro, said substitution being less than 3 substituents; cycloalkyl having at least 3 carbon atoms; substituted cycloalkyl; pyrryl; thienyl; furyl; pyridyl; piperidyl; and 3-cholesteryl.

Optical activity of the metal coordinated complex, according to this invention, resides in the phosphine or arsine ligand. This optical activity may result either from having three different groups on the phosphorus or arsenic atom or by having an optically active group attached to the phosphorus or arsenic atom.

Illustrative coordination metal complexes can be represented by the formula $M^1X_nL_3$ or $M^2X_2L_2$ wherein $M^1$ is a metal selected from the group consisting of rhodium, iridium, rutherium and osmium; $M^2$ is selected from the group consisting of palladium and platinum; X is selected from the group consisting of hydrogen, fluorine, bromine, chlorine and iodine; L is the phosphine or arsine ligand as previously defined; n is the integer one or three.

In the above coordination metal complex formulae, only one ligand (L) has to be optically active in order for the process of the reaction to be operable.

If the optical activity of the ligand resides in having an optically active group attached to the phosphorus or arsenic atom, there only has to be one such group, and the other two groups may be the same or inactive. In this instance, only one of the groups $R^5$, $R^6$ or $R^7$ has to be optically active, the remaining two groups may be identical or inactive.

Catalysts which may be used include, but are not limited to, coordination metal complexes of the following formulae. In the formulae, an asterisk indicates asymmetry, and therefore optical activity. The asterisk denotes the asymmetric atom or dissymmetric group. As an example: R* indicates the phosphorus or arsenic is asymmetric. Absence of an asterisk indicates no optical activity.

| | |
|---|---|
| (i) $M^1X(A*R^5R^6R^7)_3$ | (vi) $M^1X(AR*^5R^6R^7)(AR^5R^6R^7)_2$ |
| (ii) $M^1X(A*R^5R^6R^7)_2(AR^5R^6R^7)$ | (vii) $M^1X_3(A*R^5R^6R^7)_3$ |
| (iii) $M^1X(A*R^5R^6R^7)(AR^5R^6R^7)_2$ | (viii) $M^1X_3(A*R^5R^6R^7)_2(AR^5R^6R^7)$ |
| (iv) $M^1X(AR*^5R^6R^7)_3$ | (ix) $M^1X_3(A*R^5R^6R^7)(AR^5R^6R^7)_2$ |
| (v) $M^1X(AR*^5R^6R^7)_2(AR^5R^6R^7)$ | (x) $M^1X_3(AR*^5R^6R^7)_3$ |
| (xi) $M^1X_3(AR*^5R^6R^7)_2(AR^5R^6R^7)$ | (xiv) $M^2X_2(A*R^5R^6R^7)(AR^5R^6R^7)$ |
| (xii) $M^1X_3(AR*^5R^6R^7)(AR^5R^6R^7)_2$ | (xv) $M^2X_2(AR*^5R^6R^7)_2$ |
| (xiii) $M^2X_2(A*R^5R^6R^7)_2$ | (xvi) $M^2X_2(AR*^5R^6R^7)(AR^5R^6R^7)$ | wherein $M^1$, $M^2$, X, A, $R^5$, $R^6$, and $R^7$ are as previously defined.

It is understood that in the above illustrated list of catalysts, the dissymmetric group can be $R^5$, $R^6$ or $R^7$ and is not restricted to any one group. In addition, there may be a combination of moieties attached to the metal.

It should be understood that the above described formulae represent not only the coordinated metal complexes that contain two or three ligands, as in the formulae $M^2X_2L_2$ or $M^1X_nL_3$ respectively, but also represent those coordination metal complexes wherein the number of ligand-metal coordination bonds are described by the number of L's in the formula and wherein these bonds are provided by polydentate type ligands. For instance, although there may be only two ligands in a particular coordination metal complex, the formula $M^1X_nL_3$ still represents the complex if one of the two ligands is bidentate, i.e., it provides two coordination bonds. Likewise the formula $M^1X_nL_3$ also represents those complexes wherein there is only one ligand present if that ligand is tridentate, i.e., it provides three coordination bonds.

Substituents on the phosphorus and arsenic atoms include but are not limited to: methyl, ethyl, propyl, isopropyl, butyl and its isomers, pentyl and its isomers, hexyl and its isomers, heptyl and its isomers, octyl and its isomers, nonyl and its isomers, decyl and its isomers, undecyl and its isomers, dodecyl and its isomers, cyclopropyl, cyclobutyl, cyclopentyl, cyclohexyl, phenyl, acetoxylphenyl, methylphenyl, ethylphenyl, propylphenyl, butylphenyl, dimethylphenyl, trimethylphenyl, diethylphenyl, hydroxyphenyl, phenoxyphenyl, o-anisyl, 3-cholesteryl, benzyl, pyrryl, furyl, pyridyl, thienyl, piperidyl, menthyl, bornyl and pinyl.

A list of optically active phosphine and arsines which may be utilized includes but is not limited to: methylethylphosphine, methylisopropylphosphine, ethylbutylphosphine, isopropylisobutylphosphine, methylphenylphosphine, ethylphenylphosphine, propylphenylphosphine, butylphenylphosphine, phenylbenzylphosphine, phenylpyrrolephosphine, ethylisopropylisobutylphosphine, methylphenyl-4-methylphenylphosphine, ethylphenyl-4-methylphenylphosphine, methylisopropylphenylphosphine ethylphenyl-2,4,5-trimethylphenylphosphine, phenylbenzyl-4-dimethylaminophenylphosphine, phenylpyridylmethylphosphine, phenylcyclopentylethylphosphine, cyclohexylmethylisopropylphosphine, o-methoxyphenylmethylphenylphosphine, o-methoxyphenylcyclohexylmethylphosphine and the arsenic analogs of the above.

The optically active phosphines and arsines containing at least one phenyl group that has a substituent in the ortho position such as hydroxy; alkoxy having at least one carbon atom and a maximum of twelve carbon atoms; and aryloxy are particularly preferred compounds that are useful in the present invention. Excellent results have been obtained with methylphenyl-o-anisylphosphine and methylcyclohexyl-o-anisylphosphine. The latter compound, together with the optically active coordinated metal complex hydrogenation catalysts prepared therewith, are novel compositions of matter. It has been found that the desired enantiomorphs of substituted and unsubstituted phenylalanines are readily prepared in excellent yields when using such optically active ligands in the process of this invention.

Although only one optically active group or ligand is required in the coordination metal complex catalyst, it is preferred, for ease of preparation, that all three ligands in the above described formula, $M^1X_nL_3$, are the same. It is also preferred that asymmetry reside on either the phosphorus or arsenic atom.

It has been found that excellent yields of desired enantiomorphs can be achieved not only with the above described optically active hydrogenation catalysts which are coordination metal complexes of a metal selected from the group consisting of rhodium, iridium, ruthenium, osmium, palladium and platinum, but can also be achieved when the hydrogenation is carried out in the presence of a catalyst that comprises a solution of a metal selected from the group consisting of rhodium, iridium, ruthenium, osmium, palladium and platinum and at least one equivalent of a phosphine and/or arsine ligand per mole of metal, provided that the ligand is optically active. For instance, the catalyst can be prepared by dissolving a soluble metal compound in a suitable solvent together with a ligand wherein the ratio of ligand to metal is at least one equivalent of ligand per mole of metal, preferably two equivalents of ligand per mole of metal. Likewise, it has been found that the catalyst can be formed in situ by adding a soluble metal compound to the reaction mass together with the addition of the proper amount of the optically active ligand to the reaction mass either before or during hydrogenation.

The preferred metal to be utilized is rhodium. Soluble rhodium compounds that can be utilized include rhodium trichloride hydrate, rhodium tribromide hydrate, rhodium sulfate, organic rhodium complexes with ethylene, propylene, etc., and bis olefins such as 1,5-cyclooctadiene and 1,5-hexadiene, bicyclo-2.2.1-hepta-2,5-diene and other dienes which can form bidentate ligands, or an active form of metallic rhodium that is readily solubilized.

It has been found that the process of this invention is preferably carried out in the presence of an optically active phosphine or arsine ligand wherein the ligand is present in a ratio of about 1.5 to about 2.5 (preferably 2.0) equivalents of ligand per mole of metal. In practice, it is preferred to have the optically active catalyst in a solid form for purposes of handling and storage. It has been found that these results can be obtained with solid, cationic coordination metal complexes.

Cationic coordination metal complexes containing 2 equivalents of phosphine or arsine per mole of metal and a chelating bis olefin can be used as the catalysts in the present invention. For instance, using the organic rhodium complexes, as described above, one can prepare such cationic coordination rhodium complexes by slurrying the organic rhodium complex in an alcohol, such as ethanol, adding 2 equivalents of the optically active phosphine or arsine so that an ionic solution is formed followed by the addition of a suitable anion, such as, for instance, tetrafluoroborate, tetraphenylborate or any other anion that will result in the precipitation or crystallization of a solid cationic coordination metal complex either directly from the solution or upon treatment in an appropriate solvent.

For instance, exemplary cationic coordination metal complexes are cyclooctadiene-1,5-bis(methylcyclohexyl-o-anisylphosphine) rhodium tetrafluoroborate, cyclooctadiene-1,5-bis(methylcyclohexyl-o-anisylphosphine) rhodium tetraphenylborate and bicyclo-2.2.1-hepta-2,5-diene-bis(methylcyclohexyl-o-anisylphosphine) rhodium tetrafluoroborate.

Without prejudice to the present invention it is thought that the catalyst is present actually as a catalyst precursor and that upon contact with hydrogen the catalyst is converted to an active form. This conversion can, of course, be carried out during the actual hydrogenation of the olefinic bond or can be accomplished by subjecting the catalyst (or precursor) to hydrogen prior to addition to the olefin material to be hydrogenated.

The hydrogenation reaction is usually conducted in a solvent, such as benzene, ethanol, toluene, cyclohexane, and mixtures of these solvents. Almost any aromatic or saturated alkane or cycloaklane solvent, which is inactive to the hydrogenation conditions of this reaction, can be used. Since the hydrogenation process of this invention has been found to be specific, solvents such as nitrobenzene can also be utilized. The preferred solvent is methanol.

As noted above, the catalyst is added to the solvent either as a compound per se or as its components which then form the catalyst in situ. When the catalyst is added as its components it may be added prior to, or at the same time as the $\beta$-substituted-$\alpha$-acylamido-acrylic acid. Components for the preparation of the catalyst in situ are the soluble metal compound and the optically active phosphine or arsine ligand. The catalyst can be added in any effective catalytic amount and generally in the range of about 0.0001% to about 5% by weight of contained metal based on the $\beta$-substituted-$\alpha$-acylamido-acrylic acid and/or their salts content.

Within practical limits, means should be provided so as to avoid contacting the catalyst or reaction mass with oxidizing materials. In particular, care should be taken so as to avoid contact with oxygen. It is preferred to carry out the hydrogenation reaction preparation and actual reaction in gases (other than $H_2$) that are inert to both reactants and catalysts such as, for instance, nitrogen or carbon dioxide.

As noted hereinbefore, it has been found that the asymmetric hydrogenation is enhanced by the presence of a base in the reaction mass. Although the asymmetric hydrogenation can be carried out in a reaction mass that is free of base and even can be conducted under acidic conditions it is enhanced by the addition of a small amount, up to no more than one equivalent, of base material per mole of acrylic acid. It is surprising that a small amount of base added to even an acidic reaction mass will provide this enhanced asymmetric hydrogenation and, in fact, it has been found that the formation of a small amount of salt of the acrylic acid is sufficient to obtain these improved results.

Some bases that may be utilized are tertiary bases such as triethylamine, NaOH, and almost any other basic material that will form a salt with carboxylic acids.

After addition of the components to the solvent, hydrogen is added to the mixture until about 1 to about 5 times the mole quantity of the β-substituted-α-acylamido-acrylic acid or an amount necessary to complete the hydrogenation to the point desired has been added. The pressure of the system will necessarily vary since it will be dependent upon the type of β-substituted-α-acylamido-acrylic acid, type of catalyst, size of hydrogenation apparatus amount of components and amount of solvent and/or base. Lower pressures, including atmospheric and subatmospheric pressure, can be used as well as higher pressures.

Reaction temperatures may be in the range of about −20° C. to about 110° C. Higher temperatures may be used but are normally not required and may lead to an increase of side reactions.

Upon completion of the reaction which is determined by conventional means, the solvent is removed and the products and catalyst separated by conventional means.

Many naturally occurring products and medicaments exist in an optically active form. In these cases only one of the L or D forms is usually effective. Synthetic preparations of these compounds in the past has required an additional step of separating the products into its enantiomorphs. This process is expensive and time consuming. The process of the present invention permits the formation of optically active products thus eliminating much of the time consuming and expensive separation of enantiomorphs while improving the yield of desired enantiomorphs and reducing the yield of unwanted enantiomorphs.

Desired enantiomorphs of α-amino acids can be prepared by hydrogenating the proper β-substituted-α-acylamido-acrylic acid by the process of this invention followed by the removal of the acyl group on the α-amino and the other blocking groups by conventional means to yield the desired enantiomorph.

It has been found that the α-amino acids prepared from the β-substituted-α-acylamido-acrylic acids and-/or their salts can be readily prepared with a large predominance of the desired enantiomorph and therefore make the present invention particularly valuable.

The following examples are given to illustrate in detail how the process of this invention is carried out. It is to be understood that the specific details given in the examples are not to be construed as limiting the scope of the invention. In the following examples "parts" are by weight unless otherwise indicated. In the examples the % optical purity is determined by the following equation (it is understood that the optical activities expressed as the specific rotations are measured in the same solvent):

% Optical purity =

$$\frac{\text{observed optical activity of the mixture} \times 100}{\text{optical activity of pure enantiomorph}}$$

EXAMPLE 1

The optically active phosphines and arsines can be prepared according to the procedure of Mislow and Korpiun, J. Am. Chem. Soc. 89, 4784 (1967).

PhPCl$_2$ + 2CH$_3$OH → Ph-P(OCH$_3$)$_2$

To a suitable vessel equipped with a stirring means, a temperature measuring means and a material addition means was charged 250 parts phenyldichlorophosphine, 240 parts pyridine and 495 parts hexane. The solution was cooled to about 5°–10° C. and a mixture consisting of 96 parts methanol and 27 parts hexane was added, with stirring, over a period of about 1½ hours. The resultant mixture was stirred for an additional 2½ hours as it warmed to about 25° C. This reaction was conducted in an inert nitrogen atmosphere.

Pyridine hydrochloride, formed during the reaction, was removed by filtration and the filtrate concentrated. The yellow residue was distilled, collecting a colorless fraction boiling at 95.5°–97° C./17 mm. (82% yield of dimethylphenylphosphonite). [Harwood and Grisley, J. Am. Chem. Soc., 82, 423 (1960)]

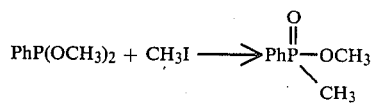

To a suitable vessel, equipped with a stirring means, a temperature measuring means and a material addition means was charged 11 parts dimethylphenylphosphonite, 2.5 parts methyl iodide and 9 parts toluene. The resultant solution was slowly heated. The reaction is exothermic and the temperature increases to about 110° C., the reaction mixture is maintained at a temperature of about 100°–120° C., and an additional 185 parts dimethylphenylphosphonite is slowly added. Additional amounts of methyl iodide, in about 1 part increments, are occasionally added during the phosphonite addition. The reaction mixture was maintained at about 110° C. for an additional hour following the addition of components. The reaction mixture was then distilled collecting the portion boiling at 148°–149° C./17 mm. (96% yield of methyl phenylmethyl phosphinate. [Harwood and Grisley J. Am. Chem. Soc., 82, 423 (1960)]

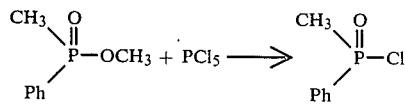

To a suitable vessel equipped with a stirring means, a condensing means, temperature measuring means and a material addition means, was charged 187 parts methyl phenylmethylphosphinate and 1600 parts carbon tetrachloride. To this mixture was added 229 parts phosphorus pentachloride in three portions of 50 parts and one portion of 79 parts. A temperature rise was observed on the addition of the first three portions. The mixture was stirred at about 60° C. for two hours and then the carbon tetrachloride and phosphorous oxychloride removed by distillation. The residue was distilled collecting the fraction boiling at 138°-141° C./17 mm. (95% yield of methylphenylphosphinic chloride). [Methoden Der Organishen Chemie (Houben-Weyl) Vol. XII/I p. 243]

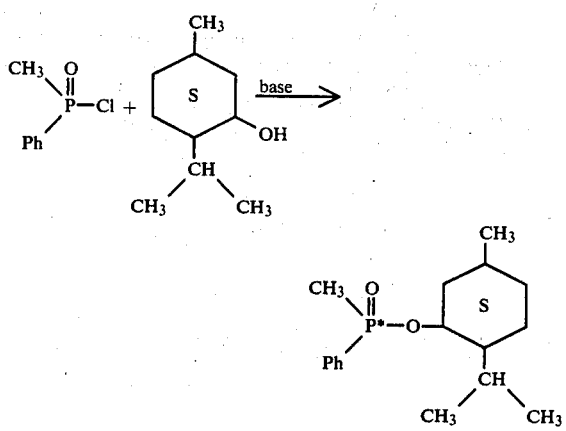

To a suitable vessel equipped with a stirring means, a condensing means, a temperature measuring means, and a material addition means, was added 78 parts l-menthol ($[\alpha]_D^{25} = -50°$ in ethanol) and 72 parts diethyl ether. To the resultant solution was added 119 parts of triethylamine and the resultant mixture cooled to about 0° C. To this mixture was added, with stirring 87 parts methylphenylphosphinic chloride over a period of about 1¼ hours while maintaining the temperature at about 0° C. The mixture was allowed to warm to about 25° C. and then heated at reflux for about 10½ hours.

The mixture was filtered to remove the triethylamine hydrochloride and the filtrate concentrated. The filtrate, upon concentration, yielded a solid melting at 50°-65° C. which is a mixture of l-menthyl methylphenylphosphinate diastereoisomers (60% S and 40% R).

The above prepared mixture of l-menthyl methylphenylphosphinate diastereoisomers was resolved by crystallization several times from hexane followed by crystallization from diethyl ether and yielded a solid that melts at 78°-82° C. which is the S form of l-menthyl methylphenylphosphinate.

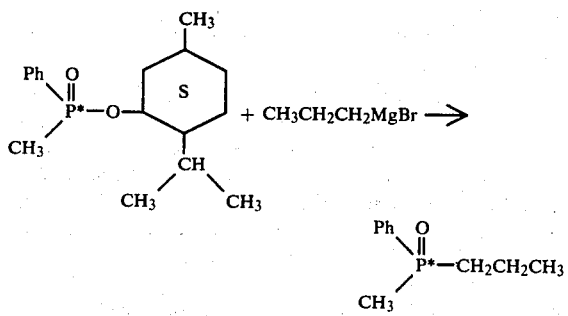

To a suitable vessel equipped with a stirring means, temperature measuring means, material addition means and a condenser means, under an inert nitogen atmosphere, was added 9.5 parts magnesium, 7 parts diethyl ether and a reaction initiating amount of iodine. A small amount of bromopropane was added to initiate the reaction and then a mixture consisting of 47 parts bromopropane and 123 parts diethyl ether was slowly added at a rate to maintain gentle refluxing of the reaction mixture. The reaction mixture was then cooled to about 25° C. and stirred for an additional two hours.

To this mixture was added a mixture consisting of 12 parts of the S form of l-menthyl methylphenylphosphinate (as prepared above) and 88 parts benzene. The diethyl ether was then removed and the resultant mixture heated at 78° C. for 64 hours.

The magnesium complex reaction product was decomposed with a solution of ammonium chloride and then filtered. The precipitate was extracted with hot benzene and the extract combined with the filtrate. The organic layer was dried over sodium sulfate and the solvents removed yielding a yellow oil. The oil was chromatographed on a silica gel column with a hexane:benzene:diethyl ether (3:1:1) mixture to yield an optically active phenylmethylpropylphosphine oxide in a 61% yield.

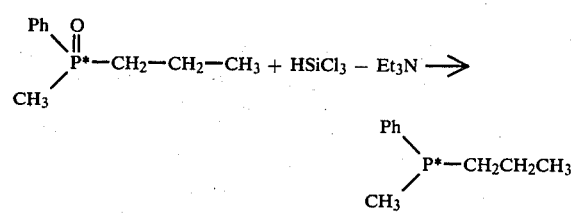

To a suitable vessel, having an inert nitrogen atmosphere, equipped with a stirring means, temperature measuring means, and a material addition means was charged 16 parts trichlorosilane and 88 parts benzene at a temperature of about 0° C. To this mixture, at a temperature of about 4°-6° C. was added a mixture consisting of 22 parts triethylamine and 44 parts benzene. The resultant mixture was then warmed to about 25° C. and a mixture consisting of 8.2 parts of optically active phenylmethylpropylphosphine oxide (as prepared above) and 22 parts benzene was added. The mixture was then heated to about 60° C. over a two-hour period and then cooled to about 25° C.

The silicon complex reaction product was decomposed with 75 parts of a 20% solution of sodium hydroxide followed by 35 parts of water. The resultant mixture was allowed to stand for about 15 hours and resulting in the layers separating. The organic layer was then extracted with 5% hydrochloric acid, twice with water and then dried over sodium sulfate. The solvent was then removed by distillation yielding methylpropylphenylphosphine in a 95% yield and having a 69% optical purity.

A preparation for rhodium III chloride tris-(methylpropylphenylphosphine) is as follows:

To a suitable vessel, having a nitrogen atmosphere, was charged 0.342 gms. (0.0013 moles) of rhodium III chloride trihydrate and 10 ml. methanol. To this was added dropwise over a 15 minute period, 0.76 gms. (0.0046 moles) of the optically active methylpropylphenylphosphine, as prepared above, in 3 ml. of methanol. The mixture was allowed to stand for 1 hour during which time a yellow precipitate separated from the solution. The precipitate was removed by filtration yielding 0.21 gms. of the rhodium complex having a specific rotation $[\alpha]_D^{25} = -69.2°$ (benzene-ethanol, 1:1 v/v).

Concentration of the filtrate yielded an additional 0.13 gms. of the product having a specific rotation $[\alpha]_D^{25} = -56.4°$(benzene-ethanol, 1:1 v/v).

EXAMPLE 2

The same general procedure of Example 1 was followed with the mixture of l-menthyl methylphenylphosphinate diastereoisomers being resolved, by crystallization, from hexane and/or hexane-ether resulting in an S form melting at 78°-82° C. having a specific rotation $[\alpha]_D^{25} = -94°$(benzene) and an R form melting at 86°-87° C. having a specific rotation $[\alpha]_D^{25} = -17°$(benzene).

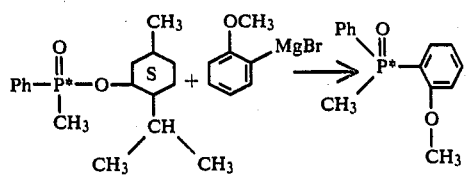

To a suitable vessel equipped with a stirring means, temperature measuring means, material addition means and a condenser means, under an inert nitrogen atmosphere was added 18.3 parts magnesium turnings, 14 parts diethyl ether and a reaction initiating amount of iodine. A small amount of o-anisylbromide was added to initiate the reaction and then a mixture consisting of 138 parts of o-bromoanisole and 400 parts diethyl ether was slowly added at a rate to maintain gentle refluxing of the reaction mixture. After completion of addition the mixture was refluxed an additional two hours.

To this mixture was added a mixture consisting of 74 parts of either the R or S form of l-menthyl methylphenyl phosphinate (the choice of S or R depends on the enantiomorph desired from the asymmetric hydrogenation) and 450 parts benzene. The diethyl ether was then removed and the resultant mixture heated at 78° C. for 64 hours.

The magnesium complex reaction product was decomposed with a solution of ammonium chloride and the product extracted from the aqueous phase with benzene. After removal of the benzene the residual oil was distilled, first removing a menthol cut and finally taking over product at 180°-190° C. and 0.5 mm. pressure. The crude methylphenyl-o-anisylphosphine oxide was formed in 60% yield. Using the R form a product with a specific rotation $[\alpha]_D^{25} = +27°$(methanol) was obtained. Use of the S form gave a product with the opposite rotation.

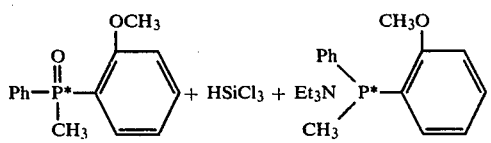

To a suitable vessel, having an inert nitrogen atmosphere, equipped with stirring means, temperature measuring means and a material addition means, was charged 16 parts of trichlorosilane and 100 parts of benzene at about 5° C. To this mixture at 4°-6° C. was added a mixture of 12 parts triethylamine and 50 parts benzene. The resultant mixture was warmed to 70° C. and a mixture of 7.5 parts optically active methylphenyl-o-anisyl phosphine oxide in 30 parts of benzene was added. The mixture was heated to 70° C. for a one hour period and then cooled to 25° C.

The silicon complex reaction product was decomposed by adding it, under nitrogen, to 75 parts of 20% sodium hydroxide at 25° C. with cooling. The desired methylphenyl-o-anisyl phosphine was obtained from the organic layer and has a specific rotation $[\alpha]_D^{25} = +41°$(methanol) when the above prepared phosphine oxide having a specific rotation $[\alpha]_D^{25} = +27°$(methanol) was used. With the opposite enantiomorph phosphine oxide the phosphine of opposite rotation was obtained.

EXAMPLE 3

Preparation of methylcyclohexyl-o-anisylphosphine

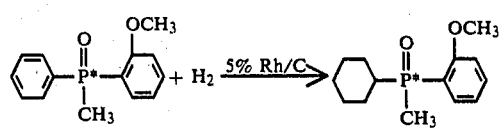

To a one liter autoclave was added 143 parts of the (+) methylphenyl-o-anisylphosphine oxide (as prepared before), 28 parts of 5% rhodium on carbon and 250 parts of methanol. The batch was heated to 75° C. and stirred under 800 psig. of hydrogen. When hydrogen uptake ceased, nmr analysis showed that the reaction illustrated by the above equation was 75% complete. A further 7.0 parts of catalyst was added, the batch repressurized to 800 psig. and the batch was run to 96% completion.

The catalyst was filtered and the methanol removed under vacuum. The crude oil was taken up in 200 parts of dibutyl ether and cooled to 0° C. The crystals which separated were filtered and washed with hexane. There was obtained 63 parts of methylcyclohexyl-o-anisylphosphine oxide melting at 108°-110° C. having a specific rotation $[\alpha]_D^{20} = +63°$(methanol).

The above phosphine oxide can be reduced to methylcyclohexyl-o-anisylphosphine in 95% yield using $HSiCl_3$ and triethylamine as described above for methylphenyl-o-anisylphosphine. The resulting methylcyclohexyl-o-anisylphosphine is a liquid having specific rotation $[\alpha]_D^{20} = +98.5°$(methanol).

EXAMPLE 4

Asymmetric hydrogenation of α-benzamido-4-hydroxy-3-methoxy-cinnamic acid

To a hydrogenation apparatus equipped with a pressure gauge, temperature measuring means and heating means, was charged 25 parts α-benzamido-4-hydroxy-3-methoxy-cinnamic acid and 186 parts methanol and 64 parts 5% sodium hydroxide. The batch was thoroughly purged to remove any traces of air and finally adjusted to 50 psig. of hydrogen and 25° C.

A catalyst solution was made by dissolving 0.0059 g. of rhodium 1,5-cyclohexadiene chloride ([Rh(1,5 hexadiene) $Cl]_2$) J. Am. Chem. Soc. 86, 217 (1964), in 2 ml. of benzene under nitrogen. Then 0.0139 g. of (+) methylphenyl-o-anisylphosphine in 1.3 ml. of benzene was added. Then hydrogen was passed through the mixture for five minutes. The resulting catalyst solution is then forced into the autoclave with hydrogen pressure. Hydrogenation begins immediately and is complete after 3 to 4 hours at 25° C. and 50 psig.

Assay of the resulting solution shows an optical purity of 56.4% corresponding to a 78/22 L/D mixture of the sodium salt of N-benzoyl-3-(4-hydroxy-3-methoxyphenyl)-alanine.

The N-benzoyl substituted amino acid can be obtained in 95% yield by evaporating off the methanol and neutralizing the sodium salt with hydrochloric acid.

The resulting L enantiomorph can be converted to L-DOPA by simple hydrolysis to remove the blocking groups, benzoyl and methyl in the 3 substituent position on the phenyl.

EXAMPLE 5

A 1 liter autoclave was charged with 25.0 g. of α-Benzamido-4-hydroxy-3-methoxy-cinnamic acid, 300 ml. of methanol and 0.6 ml. of 5% aqueous NaOH. The batch was stirred at 25° C. under 40 psi. (gauge) of pure hydrogen until it was certain there were no leaks. Then approximately 1 ml. (0.01% Rh, 0.05% phosphine) of the following catalyst solution was added through a septum without breaking pressure. [Catalyst solution made by dissolving under $N_2$ 0.0050 g. [Rh (1,5 hexadiene)Cl]$_2$ in 0.33 ml. of a solution of methylphenyl-o-anisylphosphine with a specific rotation $[\alpha]_D^{25} = +42°$-(methanol) in benzene containing 0.041 g./ml. and diluting to 1 ml. with methanol.]

A stirring rate of 1400 RPM is maintained in the reaction mass and hydrogen begins to be absorbed after a 2–5 minute induction period and the hydrogenation is completed in 2 hours.

The methanol is evaporated and the acid dissolved in one mole of aqueous NaOH. The neutral catalyst is extracted with benzene and set aside for recovery. The free amino acid is then precipitated by adding to conc. HCl with liberal seeding. There is obtained 24 g. of N-benzoyl-3-(4-hydroxy-3-methoxyphenyl)-alanine containing 73% of the L enantiomorph and 27% of the D enantiomorph. The L enantiomorph can be converted to L-DOPA by hydrolysis as in Example 4.

EXAMPLES 6–20

Other optically active α-amino acids prepared by a process using a procedure similar to the procedures of Examples 4 and 5, together with the olefinic compound hydrogenated, the phosphine ligand utilized in the rhodium catalyst and the optical purity obtained are as follows:

| Example | Olefin | Product | Catalyst (Ligand) "R" | Optical Purity % |
|---|---|---|---|---|
| 6 | CH$_2$=C(NH-C(=O)-Ph)-COOH | CH$_3$-CH(NH-C(=O)-Ph)-COOH * | CH$_3$CH$_2$CH$_2$— | 6 |
| 7 | CH$_2$=C(NH-C(=O)-CH$_3$)-COOH | CH$_3$-CH(NH-C(=O)-CH$_3$)-COOH * | o-methoxyphenyl | 32 |
| 8 | CH$_2$=C(NH-C(=O)-CH$_3$)-COOH | CH$_3$CH(NH-C(=O)-CH$_3$)-COOH * | CH$_3$CH$_2$CH$_2$— | 8 |
| 9 | Ph-CH=C(NH-C(=O)-Ph)-COOH | Ph-CH$_2$-CH(NH-C(=O)-Ph)-COOH * | CH$_3$CH$_2$CH$_2$— | 12 |
| 10 | Ph-CH=C(NH-C(=O)-Ph)-COOH | Ph-CH$_2$-CH(NH-C(=O)-Ph)-COOH * | o-methoxyphenyl | 28 |

-continued
| # | Starting material | Product | R | Yield |
|---|---|---|---|---|
| 11 | 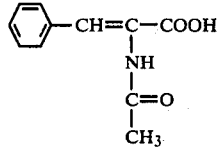 | 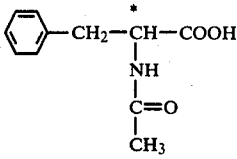 | 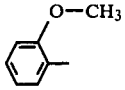 | 45 |
| 12 | 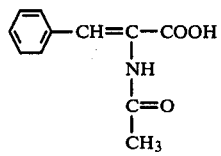 | 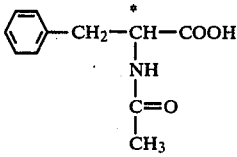 | CH₃CH₂CH₂— | 14.5 |
| 13 | 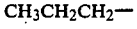 | 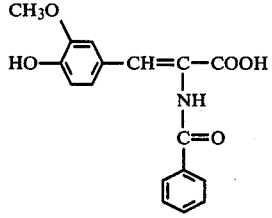 | CH₃CH₂CH— | 28 |
| 14 | 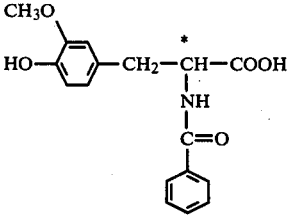 | 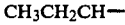 | 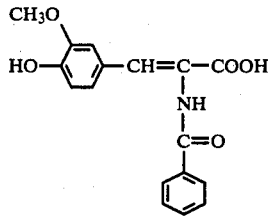 | 32 |
| 15 | 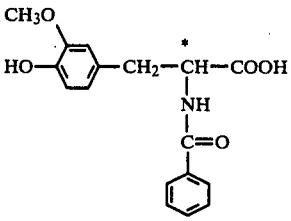 |  | 3-cholesteryl | 1.1 |
| 16 | 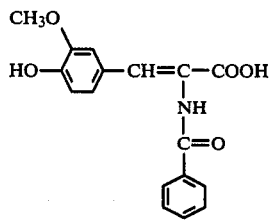 | 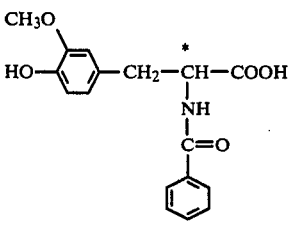 | 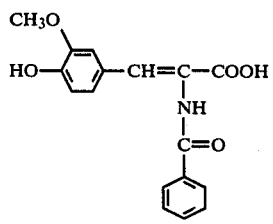 | 20 |
| 17 | 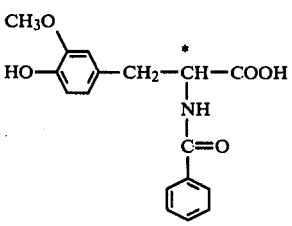 | 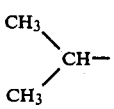 | 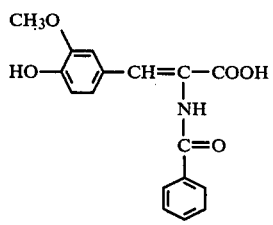 | 8 |
| 18 | 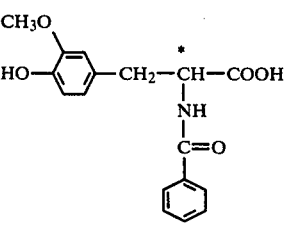 | 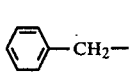 | 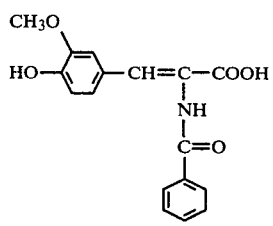 | 0.1 |

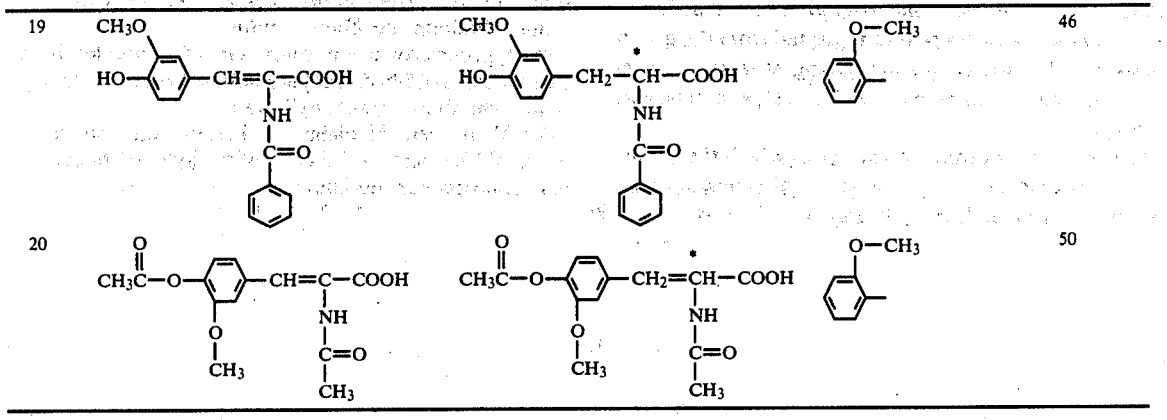

EXAMPLE 21

An autoclave was charged with 25.0 g. (0.085 moles) of α-acetamido-4-hydroxy-3-methoxy-cinnamic acid acetate, 300 ml. of methanol and 0.36 ml. of 50% NaOH. The autoclave was pressurized with a 50/50 mixture of $N_2$ and $H_2$ to 35 psig.

A catalyst solution was prepared by dissolving 0.0050 g. (0.023 meq.) of $[Rh(1,5 \text{ hexadiene})Cl]_2$ in 0.5 ml. of benzene and adding, under $N_2$, 0.051 meq. of (+) methylcyclohexyl-o-anisylphosphine (optical purity=-about 90%) in 2.4 ml. of benzene. Hydrogen was bubbled through this solution for ten minutes.

The catalyst solution was then added to the autoclave. The hydrogenation was carried out at 60° C. and was complete in 4 hours.

The product obtained by evaporation of the solvent was N-acetyl-3-(4-hydroxy-3-methoxyphenyl)-alanine acetate which had a specific rotation $[\alpha]_D^{25} = +38.2$ (Na salt in water). Pure N-acetyl-3-(4-hydroxy-3-methoxyphenyl)-L-alanine acetate, also as a sodium salt in water, had a specific rotation $[\alpha]_D^{25} = +54.0°$.

Thus, the optical purity of the resulting hydrogenation product was 70.7% or better than 85% of the L enantiomorph and 15% of the D enantiomorph.

Using a similar procedure with (−) methylcyclohexyl-o-anisylphosphine (optical purity=about 80%) resulted in a hydrogenation product containing a major amount of the D enantiomorph (optical purity of the reaction product mixture was 65%). Thus, by the proper choice of the (+) or (−) phosphine either enantiomorph can be produced in a major amount.

EXAMPLE 22

A procedure similar to example 21 was carried out using the (−) methylcyclohexyl-o-anisylphosphine as the optically active ligand and α-benzamido-4-hydroxy-3-methoxy-cinnamic acid as the β-substituted-α-acylamido-acrylic acid.

The resulting hydrogenation product was N-benzoyl-3-(4-hydroxy-3-methoxyphenyl)-alanine containing a major amount of the D enantiomorph (optical purity of the reaction product mixture=about 65%).

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

The embodiments of this invention in which a particular property or privilege is claimed are defined as follows:

1. A process which comprises hydrogenating the olefinic bond of a β-substituted-α-acylamido-acrylic acid and/or its salt in the presence of cationic coordination rhodium complexes containing 2 equivalents of an optically active phosphine or arsine ligand per mole of rhodium and a chelating bis olefin.

2. A process according to claim 1 wherein the hydrogenation is conducted in the presence of a base.

3. A process according to claim 1 wherein the β-substituted-α-acylamido-acrylic acid is represented by the structural formula:

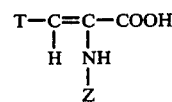

wherein, T is selected from the group consisting of hydrogen, carboxyl, unsubstituted and substituted alkyl, thienyl, β-indolyl, β-imidazolyl, furyl, piperonyl and

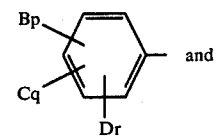

B, C and D are independently selected from the group consisting of hydrogen, alkyl, carboxyl, hydroxyl and their metal salts, alkoxy, halogen, acyloxy, aryloxy, aralkyloxy, amino, alkyl amino, nitro, cyano, Z is selected from the group consisting of substituted and unsubstituted acyl, p, q and r are integers from 0 to 5, provided that the sum of p, q and r does not exceed 5.

4. A process according to claim 3 wherein the hydrogenation is conducted in the presence of a base.

5. A process according to claim 1 in which the optically active ligand is a phosphine.

6. A process according to claim 5 in which the phosphine contains at least one phenyl group that has a substituent in the ortho position selected from the group consisting of hydroxy; alkoxy having at least one carbon atom and a maximum of twelve carbon atoms; and aryloxy.

7. A process according to claim 1 in which the β-substituted-α-acylamido-acrylic acid is a β-(substituted or unsubstituted phenyl)-α-acylamido-acrylic acid.

8. A process of claim 1 wherein said complex is cyclooctadiene-1,5-bis(methylcyclohexyl-o-anisylphosphine) rhodium tetrafluoroborate.

9. A process of claim 1 wherein said complex is cyclooctadiene-1,5-bis(methylcyclohexyl-o-anisylphosphine) rhodium tetraphenylborate.

10. A process of claim 1 wherein said complex is bicyclo-2.2.1-hepta-2,5-diene-bis(methylcyclohexyl-o-anisylphosphine) rhodium tetrafluoroborate.

* * * * *

UNITED STATES PATENT AND TRADEMARK OFFICE
CERTIFICATE OF CORRECTION

PATENT NO. : 4,261,919
DATED : April 14, 1981
INVENTOR(S) : William S. Knowles and Milton J. Sabacky It is certified that error appears in the above-identified patent and that said Letters Patent are hereby corrected as shown below:

Column 1, line 59, "ariants" should read -- variants --.

Column 3, line 40, "$AR^5R_6R^7$" should read -- $AR^5R^6R^7$ --.

Column 3, line 63, "rutherium" should read -- ruthenium --.

Column 6, line 38, "cycloaklane" should read -- cycloalkane --.

Signed and Sealed this

Fourteenth Day of July 1981

[SEAL]

Attest:

GERALD J. MOSSINGHOFF

Attesting Officer

Commissioner of Patents and Trademarks